(12) United States Patent
Krieg et al.

(10) Patent No.: US 7,683,330 B2
(45) Date of Patent: Mar. 23, 2010

(54) METHOD FOR DETERMINING POSITRON EMISSION MEASUREMENT INFORMATION IN THE CONTEXT OF POSITRON EMISSION TOMOGRAPHY

(75) Inventors: Robert Krieg, Nürnberg (DE); Rainer Kuth, Herzogenaurach (DE); Ralf Ladebeck, Erlangen (DE); Ralph Oppelt, Uttenreuth (DE); Sebastian Schmidt, Erlangen (DE); Markus Vester, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/438,209

(22) Filed: May 23, 2006

(65) Prior Publication Data

US 2006/0266947 A1    Nov. 30, 2006

(30) Foreign Application Priority Data

May 24, 2005   (DE) .................. 10 2005 023 907

(51) Int. Cl.
    *G01T 1/166* (2006.01)
(52) U.S. Cl. .................................. 250/363.04
(58) Field of Classification Search ............. 250/363.04
    See application file for complete search history.

(56) References Cited

U.S. PATENT DOCUMENTS 6,339,223 B1 *   1/2002   Motomura et al. ..... 250/363.07
7,075,087 B2 *   7/2006   Wang et al. ............ 250/363.04
2005/0226527 A1 10/2005  Weese et al.

FOREIGN PATENT DOCUMENTS

DE       102 31 061 A1     1/2004

* cited by examiner

*Primary Examiner*—David P Porta
*Assistant Examiner*—Carolyn Igyarto
(74) *Attorney, Agent, or Firm*—Harness, Dickey & Pierce, PLC

(57) ABSTRACT

A method is disclosed for determining positron emission measurement information in the context of positron emission tomography. The method includes carrying out a positron emission measurement, in a body area of a subject to be examined, to record positron emission measurement information with point resolution and determining a time frame of the measurement by, at the same time, generating images of the body area to be examined with a relatively higher time resolution and with point-resolved image data, using a second imaging method. Further, a local shift of points of individual images of the second imaging method is determined, caused by movement processes of the subject to be examined, and as a function thereof, of the positron emission measurement information for at least a part of the measurement period and of the body area to be examined. Finally, the positron emission measurement information is adjusted as a function of the determined shift.

22 Claims, 2 Drawing Sheets

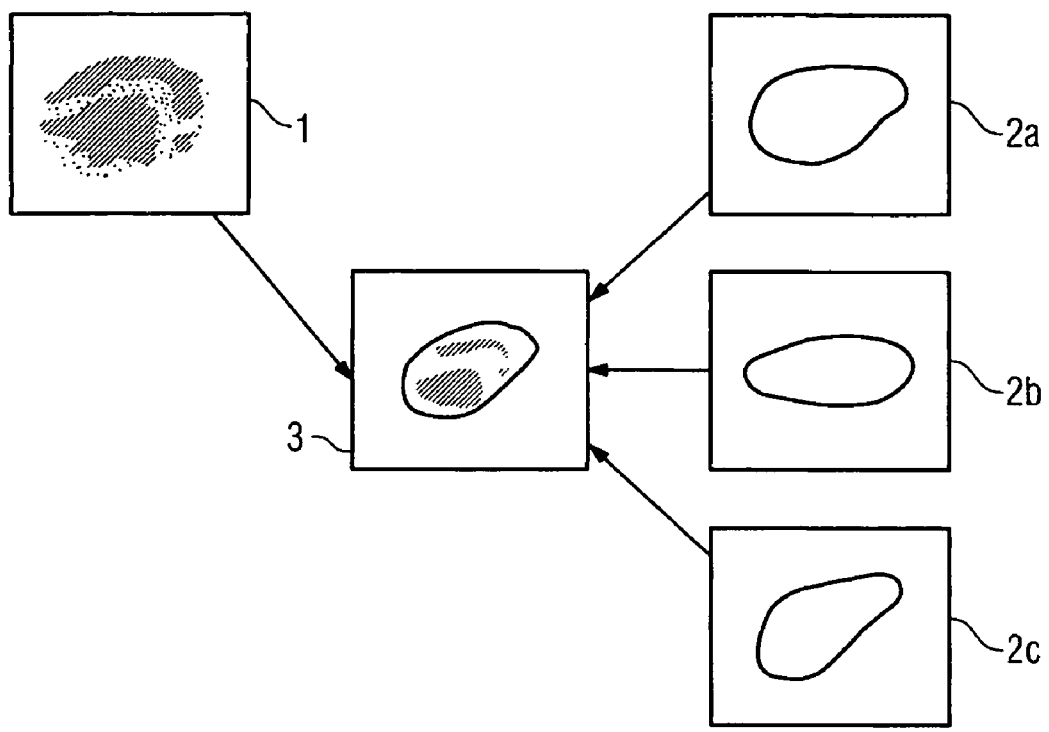
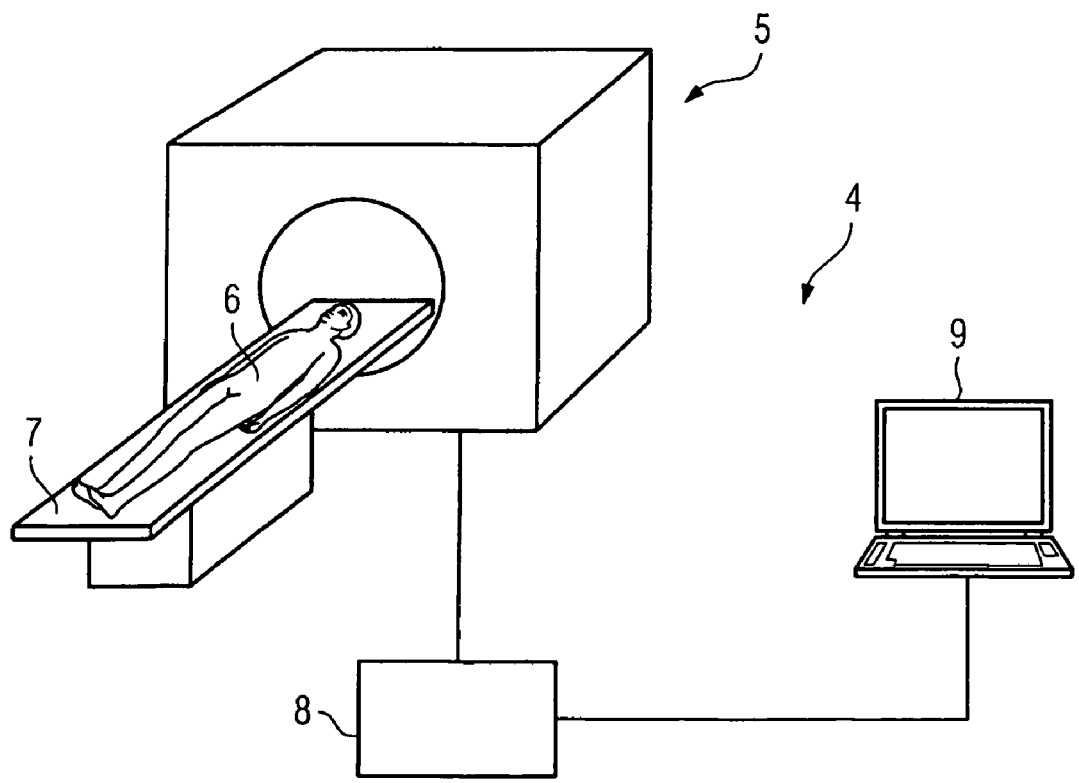

METHOD FOR DETERMINING POSITRON EMISSION MEASUREMENT INFORMATION IN THE CONTEXT OF POSITRON EMISSION TOMOGRAPHY

The present application hereby claims priority under 35 U.S.C. §119 on German patent application number DE 10 2005 023 907.2 filed May 24, 2005, the entire contents of which is hereby incorporated herein by reference.

FIELD

The invention generally relates to a method for determining positron emission measurement information in the context of positron emission tomography.

BACKGROUND

Positron emission tomography is used in particular to answer diagnostic questions concerning the function of organs, with the main focus being on metabolic processes. For this purpose, the distribution of a radioactive marker substance in the body of a subject being examined is determined.

Compared to other diagnostic methods, positron emission tomography has a somewhat poor time resolution, so that natural movement processes in the body of a subject being examined, for example peristalsis, respiration or heart beat, take place with time constants which are considerably shorter than the measurement times on which the positron emission tomography is based. This has the effect that the positron emission measurement information appears as spatially blurred points in a presented view, so that exact attribution to an anatomical feature of the examined subject is possible only with very great difficulty, if indeed at all. The informativeness of positron emission measurement in terms of structural and anatomical features is therefore limited.

SUMMARY

An object of at least one embodiment of the invention is to provide a method for determining positron emission measurement information which is improved with regard to problems of spatial blurring.

An object may be achieved by a method comprising:
  carrying out a positron emission measurement, in a body area of a subject to be examined, in order to record positron emission measurement information with point resolution,
  determining a time frame of the measurement by at the same time generating images of the body area to be examined with a high time resolution and with point-resolved image data, by means of a second imaging method,
  determining a local shift of the points of the individual images of the second imaging method, caused by movement processes of the subject being examined, and as a function thereof, of the positron emission measurement information for at least a part of the measurement period and of the body area to be examined, and
  adjusting the positron emission measurement information as a function of the determined shift.

According to at least one embodiment of the invention, therefore, a positron emission measurement is first carried out which involves introducing tracer substances into the body of the subject being examined. The positron emission measurement information can be detected with the aid of gamma detectors which respond to the radiation arising as a consequence of pair annihilation processes. Thus, over the course of the measurement, a series of positive signals are generally detected, although the individual signal information detected in such a measurement appears spatially blurred on account of the poor time resolution of at least one embodiment of the method. It is therefore difficult for this information, pointing for example to metabolic processes of cells in healthy or diseased tissue, to be attributed unambiguously to a corresponding anatomical structure in the body of the subject being examined.

According to at least one embodiment of the invention, it is proposed to determine a time frame for the measurement by at the same time producing images of the body area to be examined, or also of the whole body of the subject being examined, by way of a second imaging method which has a high time resolution compared to the positron emission measurement. The time resolution is to be chosen here in such a way that possible movement artifacts caused by the heart beat, respiration, peristalsis or other voluntary or involuntary movement processes of the subject being examined, can be resolved. It is conceivable, for example, to use an imaging method with a time resolution in the milliseconds range, that is to say much better than the resolution lying in the seconds range, which is provided by positron emission tomography. It is thus possible to achieve time resolution of processes such as the heart beat, for example.

With at least one embodiment of the second imaging method, which is expediently a noninvasive method, image data with point resolution are generated which are spatially sharp and deliver a time frame of the positron emission measurement by showing the position of anatomical structures in the examination area at different times.

Based on the shift of the individual image points of the images generated by the second method in the course of the individual recordings, movement processes of the subject being examined, for example voluntary muscle movements or respiration or the like, can be tracked. The local shift of all or some of the points of an image in the measurement period is determined, for example, with the aid of suitable image-processing software and used to obtain corresponding spatial shift information for the positron emission measurement information for the entire measurement period or for a part of the measurement period. The determined shift serves, finally, to determine adjusted positron emission measurement information, that is to say to allow the spatially blurred measurement information consisting of image points, or of signals from the positron emission measurement, to be sharply localized relative to anatomical structures obtained from the images of at least one embodiment of the second method. In the context of such adjustment, time-integration may be appropriate.

The local shift can be determined in relation to at least one normal image or a data set of normal images. For this purpose, an image or several images are selected which, with respect to the question that is to be cleared up, provide a very good or even optimal presentation of the affected structures in the body. On the basis of such normal images or certain areas of images with good resolution, it is possible to determine information on shift with the necessary or desired precision.

An image generated by at least one embodiment of the second imaging method and/or a mean image defined from several images of the examination subject or of a part thereof can be used as the normal image or for a data set of normal images. If one image is used, it can be an image that was recorded for example after approximately half of the measurement time or that can be attributed to a rest position or to particularly informative positions of the anatomical structures shown. The image can in principle be selected in any desired way from the generated images, although simple determination of the shift in the image space must be possible. Likewise, a mean image can be used which is determined by computer from several of the images or even from all of the images that have been prepared using the second imaging method. A mean image of this kind can additionally provide information in respect of the mean positioning or arrangement of the anatomical structures shown.

Of course, it is also possible to use normal images or data sets of normal images from earlier examinations of the patient, in order in this way to obtain indications of possible changes compared to a previous structure or previous functional characteristics as are determined from the positron emission tomography. The movement of individual image points can then be expediently defined relative to this normal image or the data set of normal images by way of a suitable programming.

According to at least one embodiment of the invention, the shift of all individual points can be taken into consideration, especially if the whole of the anatomical structure shown is of relevance for a diagnosis, or the shift of partial areas of the overall image points can be determined, especially in the case where the positron emission measurement information is limited in its local distribution to a partial area of an image or mean image generated with at least one embodiment of the second method.

The images obtained using at least one embodiment of the second imaging method can be generated continuously or at intervals at least during a part of the measurement period. In continuous imaging, an extensive time frame is obtained for the entire period of the positron emission measurement, such that an evaluation can make use of all the information whose recording is possible in a combination of both methods. In recording at intervals, the amount of data material recorded is limited, and it is possible to avoid costs for carrying out further imaging and to avoid placing an additional burden on the patient by carrying out further imaging. Recording images only at certain intervals may be expedient if, for example, the positron emission signals are expected to occur in a time cluster within a defined time slot of the measurement period.

The local shift is advantageously determined using transformation tables, in particular transformation tables for individual points and/or for partial areas of the body area that is to be examined. For example, for each image or each data set of images of a time slot of the measurement period, a transformation table can be defined which reflects the local shift in relation to the normal image or the normal images for all individual points or, in particular however, for particularly important partial areas of the body area that is examined. Such a data set of normal images can, as has been mentioned, be composed of several images, although it can also be a data set that belongs to a partial area of an image of particular relevance to the examination that is to be carried out. The transformation table is calculated from the available image data and reflects the shift relative to the normal data. Such a transformation table is suitable in particular for processing with computer systems or corresponding programming means with which subsequent image processing or renewed processing of the available material is possible.

The positron emission measurement information can be adjusted by being shifted back by the extent of the shift that has been determined. The spatial blurring of the individual signals from the positron emission tomography is thus reversed in the context of the reprocessing in order to permit an exact attribution to an anatomical structure in the body of the subject being examined. In the positron emission image, the individual points that form a spatially blurred area are first distributed over a wide area as a function of the movement artifacts. If the shift describing this distribution has now been defined relative to a normal image for example, the points are shifted back by the determined amount, corresponding to the position of the associated anatomical structure in the normal image. In relation to individual objects of an image presentation, this corresponds to a deformation as a function of the outer and inner shape changing in the context of the movement.

The adjusted positron emission measurement information can be presented in pictorial form, in particular in the normal image or the data set of normal images or in an image already containing positron emission measurement information, in particular in the context of image superposition or image fusion. A pictorial presentation of the recorded measurement information, after the latter has been adjusted with the aid of the shift that has been determined, facilitates the diagnosis and the evaluation of the measurement results. The pictorial presentation of the adjusted measurement information no longer contains any spatial blurring caused by poor time resolution, with the result that the recorded signals can be easily attributed.

A pictorial presentation of the measurement information can also be more easily understood than a purely numerical presentation involving, for example, provision of transformation tables or the like. The physician or medical assistant responsible for the diagnosis or for the data evaluation is able to access a data presentation with good resolution, as a result of which it is possible to avoid errors caused by incorrect attribution to an anatomical feature. Such a pictorial presentation can likewise be used for further processing by image-processing software.

The measurement information from the other imaging method can likewise be adjusted and, if appropriate, presented in pictorial form, in particular in a normal image or a data set of normal images or in an image already containing positron emission measurement information. The measurement information from at least one embodiment of the second imaging method is adjusted in respect of a normal image or a data set of normal images serving as reference, an image sequence of several images or a series of image data which can be attributed to a partial area of an image or of several images. To do this, shifting back is again possible as a function of the determined local shift, so that the anatomical structures which are in each case presented and which are to be understood in the widest sense are imaged on one another. This can also be done in respect of a reference image which has been generated earlier and which is now used as normal image. Thus, after the shifts caused by movement artifacts have been eliminated from the calculation, a series of images can be superposed or also fused, in which case it is now possible, in the form devoid of movement artifacts, to extract the relevant image information, also in respect of a time development.

Embodiments of the second imaging method used can include a magnetic resonance method and/or computed tomography method and/or ultrasound method and/or a method of optical tomography and/or a magnetic field sensor method and/or a method supplying medical measurement information convertible into images. The method uses a time resolution which is sufficient to rectify the spatial blurring arising from the positron emission measurement. Methods are suitable which permit particularly good presentation of the examination area in structural respects; that is to say in relation to the relevant anatomical structures. Anatomical structures are to be understood here as all information in respect of the examination area which can be spatially attributed, that is to say in particular pathological changes and the like.

To allow the recording with at least one embodiment of the second imaging method to be carried out without difficulty during the entire period of the positron emission measurement, a method is recommended which can be carried out without any appreciable risk of damaging the patient, for example magnetic resonance tomography. The choice of at least one embodiment of the second method also depends on a suspected disease of the patient or on the severity of such a disease, and, for embodiments of the second method, it is possible to use a combination of various imaging methods, for example a magnetic field sensor method or an ultrasound method, which can be employed simultaneously or in alternation within identical body areas or in different body areas or with a different accuracy.

The local shift can be determined directly after the end of a part of the measurement period that forms a time slot. Therefore, over a defined time period, images can be generated, or a certain number of images can be generated, after which, for example for two-dimensional slice data or a reconstructed three-dimensional data set, a local shift is determined, for example in respect of a normal image formed from the images of this slot. On the basis of this determined shift, data adjustment can be performed so that the newly recorded measurement information is expediently inserted gradually into an already existing image with positron emission measurement information, so that it becomes possible in practice to trace the measurement course almost in real time.

According to at least one embodiment of the invention, the heart beat and/or the respiration and/or voluntary and/or involuntary movements of the subject being examined may be resolved by the time resolution of at least one embodiment of the second imaging method. In this way, movements that cannot be avoided at all or that cannot be avoided over a fairly long time period can be compensated for by computing devices/methods, so that they do not lead to errors or problems in the measurement evaluation.

For application of positron emission tomography in the field of oncology, it may thus be expedient to compensate for the respiratory movements by means of suitable software, particularly in connection with imaging in the region of the thorax or abdomen. As is the case in the field of cardiology too, the use of magnetic resonance tomography is recommended here as at least one embodiment of the second imaging method. In cardiology, uncertainty caused by the constant movements of the heart can be avoided with the aid of the method according to at least one embodiment of the invention.

At least one embodiment of the method according to the invention may afford the advantage that fewer or none of the recorded measurement data have to be discarded. Overall, it is possible, using the method according to at least one embodiment of the invention, to answer diagnostic questions concerning organ functions with a greater degree of accuracy. The previous uncertainties occasioned by the spatial blurring of the positron emission measurement information may thus be avoided.

BRIEF DESCRIPTION OF THE DRAWINGS

Further advantages, features and details of the invention will become evident from the following illustrative embodiments and from the drawings, in which:

FIG. 2 shows a sketch illustrating how positron emission measurement information is adjusted as a function of a determined shift, and FIG. 3 shows a sketch of an apparatus suitable for carrying out the method according to at least one embodiment of the invention.

DETAILED DESCRIPTION OF THE EXAMPLE EMBODIMENTS

Figure 1:
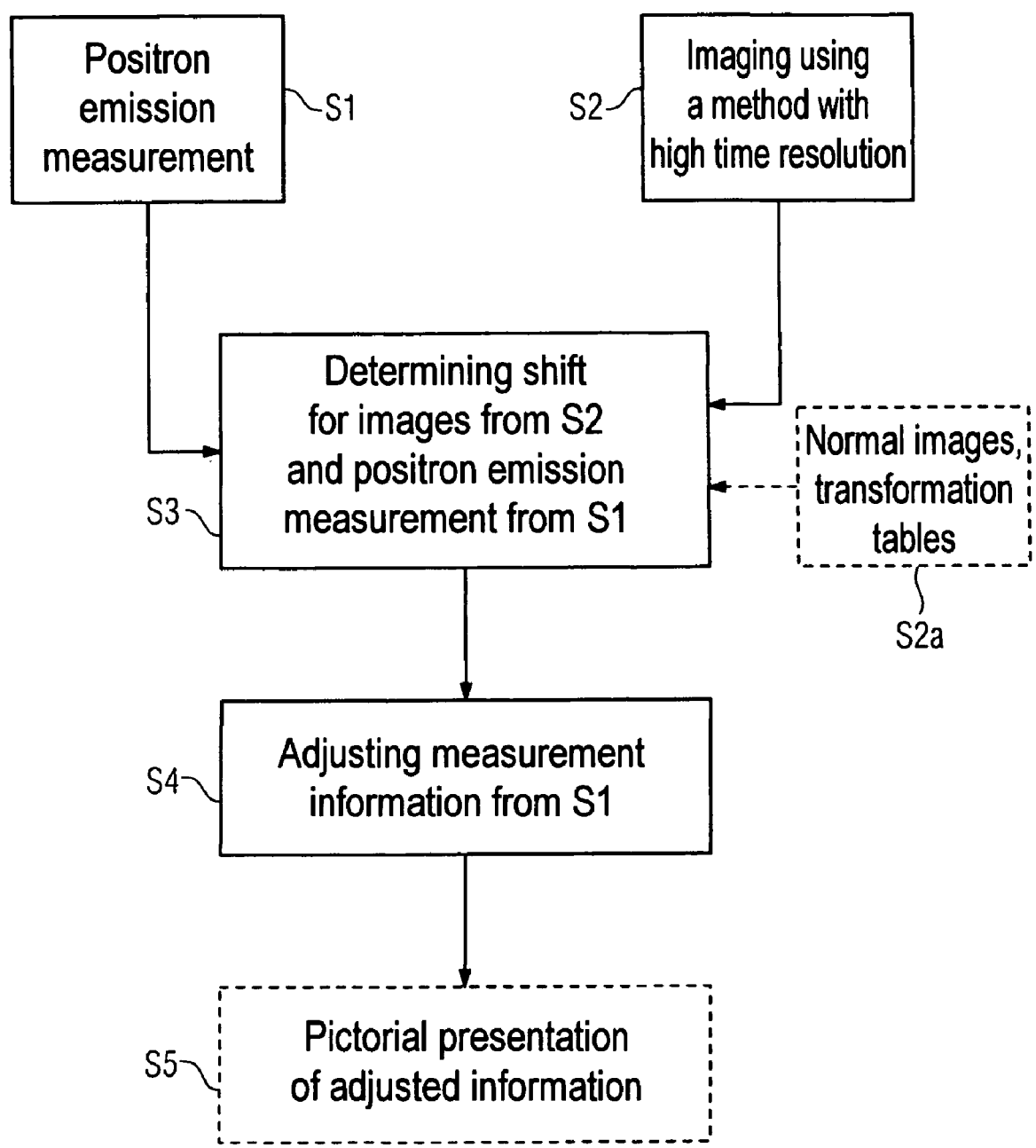
FIG. 1 shows a chart outlining the sequence of a method according to at least one embodiment of the invention.

FIG. 1 shows a chart outlining a method according to at least one embodiment of the invention comprising steps S1 to S5. In steps S1 and S2, which proceed simultaneously, a positron emission measurement is on the one hand carried out, while on the other hand a second imaging method is used to generate images with high time resolution. To carry out the positron emission measurement according to step S1, the subject being examined is administered a marker substance with radionuclides which, when positrons are emitted, interact with electrons, as a result of which gamma radiation is in turn produced.

The images prepared here continuously, during the entire period of the positron emission measurement, by at least one embodiment of the second imaging method, which has a comparatively high time resolution, are used to determine a shift for the images from steps S1 and S2, that is to say for the images from the second imaging method on the one hand and the measurement information from the positron emission measurement on the other hand, as a function of the shift initially determined for at least one embodiment of the second imaging method. Here, use is made of the fact that, when generating the images by at least one embodiment of the second method, a time frame of the measurement period was obtained with the aid of which it is now possible to trace the movement processes in the body, for example respiration or heart beat or also muscle movements.

For this purpose, as is shown in step S2a, normal images or transformation tables are used, the normal image used being a particularly typical image of a time slot of the examination. The transformation tables are calculated for each image of a time slot relative to the normal image serving as reference, and they show the shift of the individual points of the respective images in comparison with the given normal image.

Finally, in step S4, the shift determined in step S3 can be used to adjust the positron emission measurement information from step S1 in order thereby to resolve the spatial blurring and permit a clear attribution to anatomical structures. An area emerging as a blurred signal from the positron emission measurement can thus be contracted with respect to an exactly defined anatomical structuring of a normal image, or the points forming the blur are shifted back according to the movement that has taken place.

Finally, the information from the positron emission measurement is presented in pictorial form in step S5 for better evaluation. After the end of each time slot of the measurement, the newly determined data are added to an existing positron emission image, in order in this way to be able to trace the measurement almost in real time. For better attribution to anatomical structures, the positron emission measurement information is introduced into an image which permits more precise anatomical evidence and which has been obtained from images recorded in at least one embodiment of the second imaging method.

FIG. 2 shows a sketch illustrating how the positron emission measurement information is adjusted as a function of a determined shift. First, in the context of positron emission measurement, an image 1 of positron emission measurement information is prepared, while at the same time, at least one embodiment of a second imaging method is used to prepare the images 2a-2c which are attributable to the same body area of a subject to be examined as is the image 1 from the positron emission tomography. At least one embodiment of the second imaging method has a better time resolution compared to the positron emission tomography, so that, in contrast to the image 1, the anatomical structures can accordingly be clearly identified in the images 2a-2c. The image 1 is spatially blurred, by contrast. This is caused by movement processes occurring in the body of the subject being examined, for example respiration or heart beat.

With the aid of the time frame for the measurement time slot concerned, the movement processes that have taken place can be tracked and, accordingly, shifts of the individual points of the images 2a-2c, obtained by at least one embodiment of the second imaging method, are indicated. For this purpose, transformation tables are calculated which show the respective shifts of the individual points. Accordingly, the shifts for the points in the image 1 from the positron emission measurement can be tracked and, in this way, the spatial blurring of the positron emission signals can be resolved.

The positron emission measurement information forming the basis of the image 1 is adjusted as a function of the shift determined with the aid of at least one embodiment of the second imaging method, whereupon an image presentation 3 is provided which entails superpositioning of a normal image, which has been obtained as mean image from the images 2a-2c of at least one embodiment of the second imaging method, and of the adjusted positron emission measurement information according to the image 1. With the aid of the image presentation 3, the positron emission signals can be attributed unambiguously to an associated anatomical structure, as a result of which better evaluation of these data is made possible.

FIG. 3, finally, shows a sketch of an apparatus 4 suitable for carrying out a method according to at least one embodiment of the invention and including a measurement apparatus 5 which permits the recording of both positron emission measurement information and also of magnetic resonance information. The patient 6 lying on a patient bench 7 is pushed into the measurement apparatus 5 for simultaneous positron emission measurement and recording of magnetic resonance data, the measurement apparatus 5 being connected via a data link to the processing apparatus 8 which controls the recording of image data and measurement information and is responsible for presenting the information and processed images on an image display device 9.

With the aid of the time frame obtained by the magnetic resonance measurement in the examination period, it is possible to determine for the measurement information of at least one embodiment of the second imaging method and, as a function thereof, of the positron emission tomography, a local shift that reflects the movement processes in the body of the subject being examined for the measurement period. This shift is recorded in transformation tables. Typical movement processes are in this case the processes of respiration and the movements of the heart of the patient 6.

By way of the shift that has been determined with the aid of the processing apparatus 8, adjusted positron emission measurement information can be defined which is then displayed in pictorial form on the image display device 9. For this purpose, the processing apparatus 8 has access to appropriate computing capacities.

For the presentation, the newly recorded and adjusted positron emission measurement information, for each individual time slot of the measurement, is introduced into an already existing positron emission image generated after completion of the first time slot, in order in this way to permit tracking of the signals obtained across the measurement period, without having to take account of disruptive spatial blurring. An image presentation is chosen based on a normal image that was obtained with the aid of the magnetic resonance images in the first time slot. In this image, the positron emission measurement information is presented in a time-integrated format. This greatly simplifies the evaluation of positron emission measurement information, particularly in respect of its local attribution.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining positron emission measurement information in the context of positron emission tomography, comprising:

Using a first imaging method comprising: carrying out a positron emission measurement during a measurement period, in a body area of a subject to be examined, to record positron emission measurement information with point resolution, wherein said measurement period comprises a plurality of time slot intervals;

generating images of the body area to be examined with a relatively higher time resolution than said positron emission measurement and with point-resolved image data using a second imaging method during the same measurement period in which the positron emission measurement is carried out, the generated images showing a position of anatomical structures in the body area of the subject at different time slot intervals during said measurement period, wherein the generated images comprises a first image corresponding to a first time slot interval;

determining a first local shift of points for said first time slot interval by comparing said first image and a reference normal image, wherein said first local shift of points being caused by movement processes of the subject to be examined and as a function thereof; and adjusting the positron emission measurement information corresponding to said first time slot interval as a function of the determined first local shift of points.

2. The method as claimed in claim 1, wherein the local shift is determined in relation to at least one of at least one normal image and a data set of normal images.

3. The method as claimed in claim 2, wherein at least one of an image generated with the second imaging method and a mean image determined from several images is used as the at least one of at least one normal image and a data set of normal images.

4. The method as claimed in claim 1, wherein the images are generated with the second imaging method at least one of continuously and at intervals at least during a part of the measurement period.

5. The method as claimed in claim 1, wherein the local shift is determined using transformation tables.

6. The method as claimed in claim 1, wherein the positron emission measurement information is adjusted by being shifted back by the extent of the determined shift.

7. The method as claimed in claim 1, wherein the adjusted positron emission measurement information is presented in pictorial form.

8. The method as claimed in claim 1, wherein the measurement information from the other imaging method is adjusted.

9. The method as claimed in claim 1, wherein the second imaging method includes at least one of a magnetic resonance method, a computed tomography method, an ultrasound method, a method of optical tomography, a magnetic field sensor method and a method supplying medical measurement data convertible into images.

10. The method as claimed in claim 1, wherein the local shift is determined directly after the end of a part of the measurement period forming a time slot.

11. The method as claimed in claim 1, wherein the local shift is determined using transformation tables for at least one of individual points and partial areas of the body area to be examined.

12. The method as claimed in claim 1, wherein the adjusted positron emission measurement information is presented in pictorial form, at least one of in the normal image, in the data set of normal images and in an image already containing positron emission measurement information.

13. The method as claimed in claim 1, wherein the adjusted positron emission measurement information is presented in pictorial form, at least one of in the normal image, in the data set of normal images and in an image already containing positron emission measurement information, in the context of at least one of image superposition and image fusion.

14. The method as claimed in claim 1, wherein the measurement information from the second imaging method is adjusted and, if appropriate, presented in pictorial form, at least one of in the normal image, in the data set of normal images and in an image already containing positron emission measurement information.

15. The method as claimed in claim 2, wherein the second imaging method includes at least one of a magnetic resonance method, a computed tomography method, an ultrasound method, a method of optical tomography, a magnetic field sensor method and a method supplying medical measurement data convertible into images.

16. The method as claimed in claim 4, wherein the second imaging method includes at least one of a magnetic resonance method, a computed tomography method, an ultrasound method, a method of optical tomography, a magnetic field sensor method and a method supplying medical measurement data convertible into images.

17. A method, comprising:
recording positron emission measurement information with point resolution in a body area of a subject to be examined during a measurement period, wherein said measurement period comprises a plurality of time slot intervals;

generating images of the body area to be examined using another method with a relatively higher time resolution than said positron emission measurement and with point-resolved image data, during the same measurement period in which the positron emission measurement is carried out, the generated images showing a position of anatomical structures in the body area of the subject at different time slot intervals during said measurement period, wherein the generated images comprises a first image corresponding to a first time slot interval;

determining a first image shifting of points of the positron emission measurement information for said first time slot interval based upon a first individual point image shifting;

wherein said first individual point image shifting is generated by comparing said first image and a reference normal image, wherein said first individual point image shifting being caused by movement of the subject to be examined; and adjusting the recorded positron emission measurement information corresponding to said first time slot interval as a function of the determined first image shifting of points.

18. The method as claimed in claim 17, wherein the another imaging method includes at least one of a magnetic resonance method, a computed tomography method, an ultrasound method, a method of optical tomography, a magnetic field sensor method and a method supplying medical measurement data convertible into images.

19. The method as claimed in claim 17, wherein the image shift is determined using transformation tables for at least one of individual points and partial areas of the body area to be examined.

20. A computer readable medium including program segments for, when executed on a computer, causing the computer to implement the method of claim 1.

21. A computer readable medium including program segments for, when executed on a computer, causing the computer to implement the method of claim 17.

22. The method as claimed in claim 1, wherein at least one of a heart beat, respiration, and at least one of voluntary and involuntary movements of the subject being examined are resolved with the time resolution of the second imaging method.

* * * * *